United States Patent [19]

Findeisen et al.

[11] 4,455,264
[45] Jun. 19, 1984

[54] PREPARATION OF ACYL CYANIDES

[75] Inventors: Kurt Findeisen, Odenthal; Eckart Kranz, Wuppertal, both of Fed. Rep. of Germany

[73] Assignee: Bayer Aktiengesellschaft, Leverkusen, Fed. Rep. of Germany

[21] Appl. No.: 436,094

[22] Filed: Oct. 22, 1982

[30] Foreign Application Priority Data

Nov. 11, 1981 [DE] Fed. Rep. of Germany ....... 3144792
Jul. 15, 1982 [DE] Fed. Rep. of Germany ....... 3226425

[51] Int. Cl.$^3$ .................. C07C 120/00; C07C 121/34; C07C 121/76
[52] U.S. Cl. ................................ 260/545 R; 260/464; 260/465.4; 544/163; 548/128; 548/236; 548/245; 548/248; 548/255; 548/262; 548/333; 548/341; 548/530; 549/483; 560/88; 560/127; 560/196
[58] Field of Search ................ 260/545 R, 464, 465.4; 560/88, 127, 196; 544/163; 548/128, 236, 245, 248, 255, 262, 333, 341, 530; 549/483

[56] References Cited

U.S. PATENT DOCUMENTS 4,143,068  3/1979  Findeisen ........................ 260/545 R
4,238,412  12/1980  Findeisen et al. ............... 260/545 R

FOREIGN PATENT DOCUMENTS 2614241  10/1977  Fed. Rep. of Germany .

OTHER PUBLICATIONS

Herrmann et al., Synthesis No. 3, Mar. 1979, pp. 204–205.

*Primary Examiner*—Dolph H. Torrence
*Attorney, Agent, or Firm*—Spring, Horn, Kramer & Woods

[57] ABSTRACT

Acyl cyanides of the formula

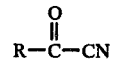

in which
R represents an optionally substituted alkyl group having 1 to 8 carbon atoms, an optionally substituted cycloalkyl group having 3 to 12 carbon atoms or an optionally substituted aryl group, or an optionally substituted 5-membered or 6-membered heterocyclic radical which additionally can be fused to a benzene ring, are obtained in high yields by reacting carboxylic acid anhydrides of the formula R—CO—O—CO—R (II) with trimethylsilyl cyanide, (CH$_3$)$_3$Si—CN (III), if appropriate in the presence of a catalyst and, if appropriate, in the presence of a diluent, at a temperature between 50° and 250° C. The acyl cyanides can be used as intermediate products, for example, for the preparation of certain herbicidally active compounds of the triazinone series.

10 Claims, No Drawings

PREPARATION OF ACYL CYANIDES

The present invention relates to an unobvious process for the preparation of certain acyl cyanides, some of which are known.

The acyl cyanides produced according to the invention can be used as starting materials for the synthesis of herbicides.

The reaction of benzoic acid anhydride with an equivalent amount of potassium cyanide, benzoyl cyanide being obtained in low yield (approx. 10% of theory), has already been disclosed (see Liebigs Annalen der Chemie 287, page 306 (1895)). The benzoyl cyanide must be extracted, using ether, from the viscous, very strongly resinified, dark brown mass formed as the main product. This process is completely unsuitable industrially, since not only does the extraction of ether lead to difficulties which are insurmountable industrially, but there is no further use for the very strongly resinified, dark brown mass. This process is thus only a possible way of forming benzoyl cyanide.

Furthermore, it has been disclosed that acyl cyanides are obtained in good yields, using carboxylic acid anhydrides as starting materials, when the carboxylic acid anhydrides are reacted either with anhydrous hydrocyanic acid or—under certain process conditions which are improved compared to the abovementioned publication—with alkali metal cyanides (see, for example, DE-OS (German Published Specification) No. 2,614,241 and DE-OS (German Published Specification) No. 2,642,199).

However, the last-mentioned processes are not free of disadvantages: when alkali metal cyanides are used, a salt residue is formed during the reaction and can be removed only with difficulty, and, in addition, the transfer of heat is made difficult. When hydrocyanic acid is used, the conventional, expensive safety measures must be taken, in particular owing to the extreme toxicity and the low boiling point.

The present invention now provides a process for the production of an acyl cyanide of the general formula $$\underset{R-C-CN}{\overset{O}{\|}} \quad (I)$$

in which

R represents an optionally substituted alkyl group having 1 to 8 carbon atoms, an optionally substituted cycloalkyl group having 3 to 12 carbon atoms or an optionally substituted aryl group, or an optionally substituted 5-membered or 6-membered heterocyclic radical which additionally can be fused to a benzene ring, characterized in that a carboxylic acid anhydride of the general formula $$\underset{R-C-O-C-R}{\overset{O}{\|}\phantom{-O-}\overset{O}{\|}} \quad (II)$$

in which

R has the meaning given above, is reacted with trimethylsilyl cyanide, (CH$_3$)$_3$Si—CN (III), if appropriate in the presence of a catalyst and, if appropriate, in the presence of a diluent, at a temperature between 50° and 250° C.

The acyl cyanides of formula (I) are obtained in very high yield and excellent purity by the process of the invention.

It is particularly surprising that acyl cyanides of the formula (I) are obtainable in high yield by the novel process according to the invention, and can be purified by simple distillation. The new process simultaneously avoids the disadvantages, which have been mentioned, of the previously known processes. The new process is not restricted to the synthesis of a few particular compounds but can be applied very widely.

The trimethylsilyl esters formed in the course of the reaction can be separated from the resulting acyl cyanides either by distillation or by chemical routes (see below).

If benzoic acid anhydride is reacted with trimethylsilyl cyanide, the course of the reaction can be represented by the following equation:

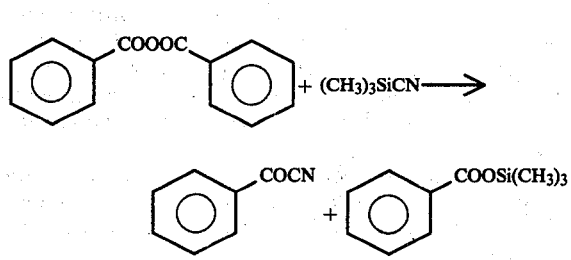

Preferred carboxylic acid anhydrides of formula (II) used as starting materials in the process according to the present invention are those in which R represents a straight-chain or branched alkyl group having 1 to 4 carbon atoms, substituted by a substituent(s) selected from alkoxy, having 1 to 4 carbon atoms, carbalkoxy having 1 to 4 carbon atoms in the alkoxy group, nitro, cyano and halogen (such as fluorine, chlorine, bromine or iodine); represents a cycloalkyl group which has 5 or 6 carbon atoms in the ring system and is optionally substituted by substituent(s) selected from alkyl, alkoxy or carbalkoxy, each having up to 4 carbon atoms, nitro, cyano and halogen (such as fluorine, chlorine and bromine); represents an aryl group (especially a phenyl or naphthyl group), which is optionally substituted by substituent(s) selected from alkyl, alkoxy or carbalkoxy, each having up to 4 carbon atoms, nitro and halogen (such as fluorine, chlorine and bromine); or represents a 5-membered or 6-membered heterocyclic radical which can contain 1 to 3 hetero-atoms (such as oxygen, sulphur and/or nitrogen) in the ring and additionally can be fused to a benzene ring, and which is optionally substituted by substituent(s) selected from alkyl, alkoxy or carbalkoxy, each having up to 4 carbon atoms, nitro, cyano and halogen (such as fluorine, chlorine or bromine).

The following may be mentioned as examples of particularly suitable heterocyclic radicals: morpholinyl, imidazolyl, pyrazolyl, pyrrolyl, isoxazolyl, piperidinyl, oxazolyl, 1,2,4-triazol-1-yl, 1,2,4-triazol-4-yl, 1,2,3-triazolyl, 1,2,4-thiadiazol-2-yl, benzimidazolyl and furanyl.

The following may be mentioned individually as preferred examples of carboxylic acid anydrides of the formula (II): acetic acid anhydride, propionic acid anhydride, pivalic acid anhydride, cyclohexanecarboxylic acid anhydride, benzoic acid anhydride, m-chlorobenzoic acid anhydride, 3,5-dichlorobenzoic acid anhydride, naphthalene-1-carboxylic acid anhydride and 1-phenyl-pyrazol-5-one-3-carboxylic acid anhydride. The aromatic carboxylic acid anhydrides, in particular benzoic acid anhydride, and pivalic acid anhydride may be mentioned as carboxylic acid anhydrides which are particularly preferred reactants for the process according to the invention.

The carboxylic acid anhydrides for the formula (II) are known or can be prepared according to generally known processes.

Trimethylsilyl cyanide, $(CH_3)_3Si—CN$ is likewise known (see, for example, Synthesis 1979, pages 522 and 523, and also U.S. Pat. No. 4,328,351).

Any of the inert organic solvents which do not undergo a chemical reaction either with the carboxylic acid anhydrides or with the trimethylsilyl cyanide, are suitable as diluents which can be employed in carrying out the process according to the invention. Examples of such solvents are the xylenes (such as o-xylene), chlorobenzene, o-dichlorobenzene, the trichlorobenzenes, nitrobenzene and tetramethylenesulphone. An excess of carboxylic acid anhydride (II) is particularly suitable as the diluent. However, it is also possible in principle to carry out the reaction according to the invention without a diluent.

The reaction temperature can be varied within the relatively wide range between 50° and 250° C., preferably between 70° and 230° C., in particular between 80° and 200° C.

The reaction is carried out in general under normal pressure. However, when low-boiling, aliphatic carboxylic acid anhydrides are used, a slight excess pressure, in general up to 10 bar, preferably from 2 to 6 bar, is advantageous.

The reaction can be accelerated by the addition of catalytic amounts of a Lewis acid. The following may be mentioned as examples of suitable Lewis acids: zinc chloride, zinc iodide, zinc cyanide, copper(I) cyanide and aluminum chloride.

The reaction can particularly advantageously be catalyzed by adding bases. Suitable bases are in particular tertiary amines such as triethylamine or 1,4-diazabicyclo-(2,2,2)-octane, salts of weak carbocyclic acids such as for example sodium acetate, sodium cyanide, potassium cyanide or sodium bicarbonate, furthermore alcoholates such as sodium methylate or potassium t-butylate.

In carrying out the process according to the invention, in general stoichiometric amounts of carboxylic acid anhydride are reacted with trimethylsilyl cyanide. However, the acid anhydride can also be used in excess, advantageously even as the solvent in this case.

The catalyst is generally used in amounts of 0.001-0.1 mol, preferably 0.005-0.05 mol, per mol of carboxylic acid anhydride (II) or trimethylsilyl cyanide (III).

The working-up is effected after the end of the reaction, customarily by distillation and, if appropriate, recrystallization.

The mixture of the carboxylic acid anhydride and the trimethylsilyl cyanide can also be reacted according to the invention in the gas phase.

In a particular embodiment, the process according to the invention can also be carried out continuously.

The trimethylsilyl carboxylates of the formula (IV) which are formed in addition to the acyl cyanides of the formula (I) in the process according to the invention can be converted back into the starting anhydrides of the formula $R—CO—O—CO—R$ (II), according to a process which does not form part of the prior art (and which is the subject of a separate application), by reaction with the acid chlorides of the formula $R—COCl$ (V) which are derived from the same carboxylic acid $(R—COOH)$ in each case. Trimethylsilyl chloride, $(CH_3)_3SiCl$ (VI), is formed as a further reaction product in this procedure, and can in turn be employed for the preparation of trimethylsilyl cyanide of formula (III):

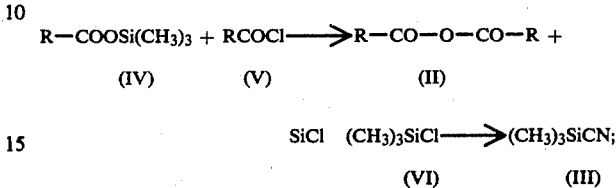

in these formulae,

R in each case has the meaning given above.

If the boiling points of the acyl cyanides of formula (I) formed in carrying out the process according to the invention, and of the trimethylsilyl esters of formula (IV), are too close together, it can be particularly advantageous to convert the latter into the starting anhydrides by reacting the reaction mixture with the appropriate acid chloride, whereby a product mixture is obtained which essentially comprises the carboxylic acid anhydride of formula (II), the desired acylcyanide of formula (I) and trimethylsilyl chloride of formula (VI), and which can be very readily separated by distillation.

The acyl cyanides of the formula (I) which can be prepared by the process according to the invention are valuable starting materials, for example, for the synthesis of 1,2,4-triazin-5-ones, which possess outstanding herbicidal properties (see, for example, German Offenlegungsschrift (German Published Specification) No 2,224,161).

Thus, for example, 3-methyl-4-amino-6-phenyl-1,2,4-triazin-5-one (common name: metamitrone) of the formula

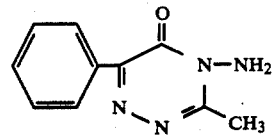

can be prepared, using benzoyl cyanide as the starting material, by a known process in which, in a first stage, benzoyl cyanide is reacted with ethanol in the presence of concentrated hydrochloric acid, and the resulting phenylglyoxylic acid ethyl ester is brought to reaction, in a second stage, with acetylhydrazine to form 1-(phenylglyoxylic acid ethyl ester)-2-acetylhydrazone, which is converted using hydrazine hydrate in the presence of pyridine into the abovementioned end product, in a third stage.

The pivaloyl cyanide obtainable according to the invention can be converted by processes which are likewise known, for example into the herbicidally active compound 3-methylthio-4-amino-6-tert.-butyl-1,2,4-triazin-5(4H)-one (common name: metribuzin) (see, for example, German Pat. No. 1,795,784, DE-OS (German Published Specification) No. 2,733,180, U.S. Pat. No. 4,175,188, U.S. Pat. No. 4,345,100, DE-OS (German Published Specification) No. 3,003,541 and DE-OS German Published Specification) No. 3,009,043).

The examples which follow illustrate the invention further.

EXAMPLE 1

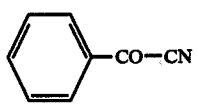

(1)

226 g of benzoic acid anhydride (1 mol) are heated to 160° C. in a 500 ml four-necked flask equipped with a stirrer, thermometer, reflux condenser and dropping funnel, and 104 g of trimethylsilyl cyanide (1.05 mols) are added dropwise in the course of two hours. After the end of the reaction, the internal temperature is increased to 200° C. for a short time, and the mixture is then fractionally distilled over a column. Yield: 126 g (=96% of theory) of benzoyl cyanide; melting point: 31° C.

EXAMPLE 2

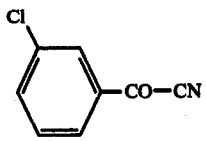

(2)

As described above, 295 g of 3-chlorobenzoic acid anhydride (1 mol) are heated to 150° C., and 1 g of zinc chloride is added. 99 g of trimethylsilyl cyanide (1 mol) are added dropwise at this temperature in the course of 90 minutes. The internal temperature is kept at 180° C. for a short time until the reaction is complete, and the mixture is then fractionally distilled.

Yield: 154 g of 3-chlorobenzoyl cyanide (=93% of theory); boiling point 118°–120° C. at 18 mbar.

EXAMPLE 3

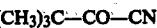

(3)

As described above, 186 g of pivalic acid anhydride (1 mol) are warmed to 180° C., 0.3 g of aluminum chloride is added, and 99 g of trimethylsilyl cyanide (1 mol) are added dropwise in the course of three hours. During this procedure, the internal temperature gradually falls to 130° C. An IR spectroscopic investigation shows that pivalic acid anhydride is no longer present. The yield of pivaloyl cyanide is 99% of theory, according to the gas chromatogram.

Working-up:

In order to facilitate the separation of the pivaloyl cyanide from the trimethylsilyl pivalate, 120.5 g of pivalic acid chloride (1 mol) are added dropwise to the above reaction mixture at 110° C. in the course of three hours. The mixture is stirred for a further thirty minutes, and is fractionally distilled. Yield: 105.5 g of pivaloyl cyanide (=96% of theory) Boiling point 121° C. at 990 mbar.

In addition, trimethylsilyl chloride and pivalic acid anhydride are obtained in almost quantitative yield.

The acyl cyanides listed in the table below can also be prepared analogously to those Examples 1–3.

TABLE 1

| Compound No. | Carboxylic acid anhydride (II) | Acyl cyanide (I) | Yield (%) | Boiling point (b.p.) Melting point (m.p.) |
|---|---|---|---|---|
| 4 | (CH₃—CO)₂O | CH₃COCN | 25 | B.p. 93° C. |
| 5 | ((CH₃)₂CH—CO)₂O | (CH₃)₂CH—COCN | 89 | B.p. 116–118° C. |
| 6 | (CH₃OCH₂—C(CH₃)₂—CO)₂O | CH₃OCH₂—C(CH₃)₂—COCN | 91 | B.p. 62–64° C./16 mbar |
| 7 | (ClCH₂—C(CH₃)₂—CO)₂O | ClCH₂—C(CH₃)₂—COCN | 88 | B.p. 62–65° C./16 mbar |
| 8 | (FCH₂—C(CH₃)₂—CO)₂O | FCH₂—C(CH₃)₂—COCN | 94 | B.p. 147–151° C. |

TABLE 1-continued

| Compound No. | Carboxylic acid anhydride (II) | Acyl cyanide (I) | Yield (%) | Boiling point (b.p.) Melting point (m.p.) |
|---|---|---|---|---|
| 9 | (cyclohexyl-H-CO)₂O | cyclohexyl-H-COCN | 82 | B.p. 79–81° C./ 18 mbar |
| 10 | (4-Cl-C₆H₄-CO)₂O | 4-Cl-C₆H₄-COCN | 94 | B.p. 114–116° C./ 18 mbar M.p. 40° C. |
| 11 | (4-H₃C-C₆H₄-CO)₂O | 4-H₃C-C₆H₄-COCN | 92 | B.p. 112–114° C./ 18 mbar M.p. 50–51° C. |
| 12 | (4-O₂N-C₆H₄-CO)₂O | 4-O₂N-C₆H₄-COCN | 84 | M.p. 116.5° C. |
| 13 | (4-H₃CO-C₆H₄-CO)₂O | 4-H₃CO-C₆H₄-COCN | 99 | B.p. 102–104° C./ 0.1 mbar M.p.: 60–61° C. |

EXAMPLE 4

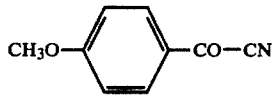  (13)

143 g (0.5 mol) of 4-methoxy-benzoic acid anhydride, 49.5 g (0.5 mol) of trimethylsilyl cyanide and 1 ml of triethylamine are mixed and stirred for 1 hour at 40°–50° C. The reaction products are then worked up by distillation.

Yield according to the gas chromatogram:

79.3 g of 4-methoxybenzolcyanide (=98.5% of theory); boiling point 102°–104° C./0.1 mbar, melting point 60°–61° C. In addition the corresponding amount of 4-methoxy-benzoic acid-trimethylsilyl ester (yield: 98% of theory) is obtained.

In the same way as in Example 4 the acyl cyanides listed in following Table 2 can also be prepared:

TABLE 2

| Compound No. | acyl cyanide (I) | yield (%) | boiling point | melting point |
|---|---|---|---|---|
| 1 | C₆H₅—COCN | 97 | 91–92° C./ 14 mbar | 31–32° C. |
| 10 | 4-Cl-C₆H₄—COCN | 93 | 114–116° C./ 18 mbar | 40° C. |
| 12 | 4-O₂N-C₆H₄—COCN | 81 | — | 116.5° C. |
| 11 | 4-CH₃-C₆H₄—COCN | 91 | 112–114° C./ 18 mbar | 50–51° C. |
| 3 | (CH₃)₃C—COCN | 98 | 121° C./ 990 mbar | — |

EXAMPLE 5

(CH₃)₃C—CO—CN     (3)

93 g (0.5 mol) of pivalic acid anhydride and 1 g of sodium cyanide are initially introduced and 49.5 g (0.5 mol) of trimethylsilyl cyanide are added dropwise. The reaction mixture is worked up by distillation. Yield: 56 g of pivaloyl cyanide (=98.9% of theory). Boiling point: 121°–125° C. In addition, pivalic acid-trimethylsilyl ester is obtained in a corresponding amount (98% of theory).

EXAMPLE 6

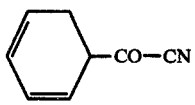
(1)

113 g (0.5 mol) of benzoic acid anhydride and 1 g of 1,4-diazabicyclo-(2,2,2)octane are initially introduced; 49.5 g (0.5 mol) of trimethylsilyl cyanide are added dropwise at a maximum of 40° C. The mixture is stirred for 4 hours at room temperature and produces the following yields according to the gas chromatogram: 88.5% of theory of benzoyl cyanide and 97.0% of theory of benzoic acid trimethylsilyl ester.

EXAMPLE 7

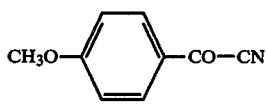
(13)

143 g (0.5 mol) of 4-methoxy-benzoic acid anhydride, 1 g of sodium cyanide (NaCN) and 49.5 g (0.5 mol) of trimethylsilylcyanide are brought together and stirred for 30 minutes at room temperature. The yields are according to the gas chromatogram: 98.5% of theory of 4-methoxybenzoylcyanide and 99.0% of theory of 4-methoxy-benzoic acid trimethylsilyl ester.

It will be appreciated that the instant specification and examples are set forth by way of illustration and not limitation, and that various modifications and changes may be made without departing from the spirit and scope of the present invention.

We claim:

1. A process for the production of an acyl cyanide of the formula

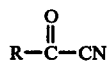

in which
R is an optionally substituted alkyl group having 1 to 8 carbon atoms, an optionally substituted cycloalkyl group having 3 to 12 carbon atoms or an optionally substituted aryl group, or an optionally substituted 5-membered or 6-membered heterocyclic radical which additionally can be fused to a benzene ring,
comprising reacting a carboxylic acid anhydride of the formula

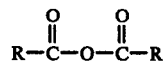

with trimethylsilyl cyanide of the formula $(CH_3)_3Si-CN$ at a temperature between about 50° and 250° C.

2. A process according to claim 1, in which R is an alkyl group having 1 to 4 carbon atoms, optionally substituted by a substituent(s) selected from alkoxy having 1 to 4 carbon atoms, carbalkoxy having 1 to 4 carbon atoms in the alkoxy group, nitro, cyano and halogen; a cycloalkyl group which has 5 or 6 carbon atoms in the ring system and is optionally substituted by substituent(s) selected from alkyl, alkoxy or carbalkoxy, each having up to 4 carbon atoms, nitro, cyano, fluorine, chlorine and bromine; a phenyl or naphthyl group, which is optionally substituted by substituent(s) selected from alkyl, alkoxy or carbalkoxy each having up to 4 carbon atoms, nitro and fluorine, chlorine and bromine; or a 5-membered or 6-membered heterocyclic radical which can contain 1 to 3 oxygen, sulphur and/or nitrogen atoms in the ring and additionally can be fused to a benzene ring, and which is optionally substituted by substituent(s) selected from alkyl, alkoxy or carbalkoxy each having up to 4 carbon atoms, nitro, cyano, fluorine, chlorine and bromine.

3. A process according to claim 1, wherein the carboxylic acid anhydride is benzoic acid anhydride or pivalic acid anhydride.

4. A process according to claim 1, wherein the reaction is carried out at a temperature between about 70° and 230° C.

5. A process according to claim 4, wherein the reaction is carried out at a temperature between about 80° and 200° C.

6. A process according to claim 1, wherein the carboxylic acid anhydride and the trimethylsilyl cyanide are employed in approximately stoichiometric amounts.

7. A process according to claim 1, wherein the reaction is carried out in the presence of a Lewis acid or a base as catalyst.

8. A process according to claim 1, wherein the reaction is carried out in the presence of a diluent.

9. A process according to clam 8, wherein the diluent is an organic solvent which is inert towards the carboxylic acid anhydride and the trimethylsilyl cyanide.

10. A process according to claim 3, wherein the carboxylic acid anhydride and the trimethylsilyl cyanide are employed in approximately stoichiometric amounts, and the reaction is carried out at a temperature between about 80° and 200° C. in the presence of a Lewis acid or a base as catalyst and in the presence of an organic solvent which is inert towards the carboxylic acid anhydride and the trimethylsilyl cyanide.

* * * * *

UNITED STATES PATENT AND TRADEMARK OFFICE
CERTIFICATE OF CORRECTION

PATENT NO. : 4,455,264
DATED : June 19, 1984
INVENTOR(S) : Kurt Findeisen et al

It is certified that error appears in the above-identified patent and that said Letters Patent is hereby corrected as shown below:

Col. 4, line 15          Before "SiCl" first instance, insert $--(CH_3)_3--$

Col. 8, Compound 12, last column          Before "116.5°C" insert --:--

Signed and Sealed this

Sixth Day of November 1984

[SEAL]

Attest:

GERALD J. MOSSINGHOFF

Attesting Officer      Commissioner of Patents and Trademarks